(12) United States Patent
Clark et al.

(10) Patent No.: US 7,022,978 B2
(45) Date of Patent: Apr. 4, 2006

(54) METHOD AND APPARATUS INCLUDING IN-RESONATOR IMAGING LENS FOR IMPROVING RESOLUTION OF A RESONATOR-ENHANCED OPTICAL SYSTEM

(75) Inventors: Bryan Clark, Mountain View, CA (US); Andrei Brunfeld, Cupertino, CA (US)

(73) Assignee: Xyratex Technology Limited, Havant-Hampshire (GB)

( * ) Notice: Subject to any disclaimer, the term of this patent is extended or adjusted under 35 U.S.C. 154(b) by 309 days.

(21) Appl. No.: 10/644,243

(22) Filed: Aug. 20, 2003

(65) Prior Publication Data

US 2004/0037175 A1 Feb. 26, 2004

Related U.S. Application Data

(63) Continuation-in-part of application No. 10/002,425, filed on Oct. 23, 2001, now Pat. No. 6,714,295, and a continuation-in-part of application No. 09/933,225, filed on Aug. 20, 2001, now Pat. No. 6,653,649, and a continuation-in-part of application No. 09/871,512, filed on May 30, 2001, now Pat. No. 6,700,840.

(51) Int. Cl.
*H01J 3/14* (2006.01)
*H01J 40/14* (2006.01)
*H01J 5/16* (2006.01)

(52) U.S. Cl. .................. 250/234; 250/216; 359/317

(58) Field of Classification Search ........ 250/234–236, 250/216, 201.5, 559.11, 559.22, 559.4, 559.45; 356/237.2; 369/44.14, 44.23, 47.1, 112.01, 369/275.1; 359/237–324
See application file for complete search history.

(56) References Cited

U.S. PATENT DOCUMENTS

| 3,901,597 | A | | 8/1975 | White |
| 4,659,224 | A | | 4/1987 | Monchalin |
| 5,220,403 | A | | 6/1993 | Batchelder et al. |
| 6,150,666 | A | * | 11/2000 | Engelhardt et al. .... 250/559.22 |
| 6,847,029 | B1 | * | 1/2005 | Hill ........................... 250/216 |

* cited by examiner

*Primary Examiner*—Stephone B. Allen
*Assistant Examiner*—Patrick J. Lee
(74) *Attorney, Agent, or Firm*—A. Mitchell Harris; Weiss, Moy & Harris, P.C.

(57) ABSTRACT

A method and apparatus including in-resonator imaging lens for improving resolution of a resonator-enhanced optical system provides resolution improvements for optical inspection and measurement systems, optical storage and retrieval systems as well as other optical systems. An imaging lens is incorporated in the resonator to image a point or area of one of the reflective surfaces of the resonator on a point or area of another reflective surface of the resonator. Resonance may be supported between the two surfaces, or with respect to only one surface with the other surface acting as an intermediary reflector. The partially reflective surface or a totally reflective surface may also be incorporated on a planar outside surface of the imaging lens.

28 Claims, 6 Drawing Sheets

METHOD AND APPARATUS INCLUDING IN-RESONATOR IMAGING LENS FOR IMPROVING RESOLUTION OF A RESONATOR-ENHANCED OPTICAL SYSTEM

RELATED APPLICATIONS

This application is a continuation-in part of U.S. patent applications "OPTICAL STORAGE METHOD AND APPARATUS HAVING ENHANCED RESOLUTION", Ser. No. 09/871,512, filed May 30, 2001 U.S. Pat. No. 6,700,840; "OPTICAL MEASUREMENT AND INSPECTION METHOD AND APPARATUS HAVING ENHANCED OPTICAL PATH DIFFERENCE DETECTION", Ser. No. 09/933,225, filed Aug. 20, 2001 U.S. Pat. No. 6,653,649; and "OPTICAL INSPECTION METHOD AND APPARATUS HAVING AN ENHANCED HEIGHT SENSITIVITY REGION AND ROUGHNESS FILTERING" Ser. No. 10/002,425, filed Oct. 23, 2001 U.S. Pat. No. 6,714,295. The specifications of all of the above-listed parent applications are incorporated herein by reference.

BACKGROUND OF THE INVENTION

1. Field of the Invention

This invention relates to optical systems, and more specifically, to an optical system incorporating a resonator to enhance the resolution of optical inspection systems and other optical devices.

2. Description of the Related Art

Optical measurement systems, optical storage and retrieval systems and other optical systems may be limited by many factors, including effective detector and illumination resolution. The effective resolution of a detection system is often set by the diffraction limitations of the system. The above-incorporated patent applications disclose techniques for enhancing the performance of a variety of optical systems and improving the resolution of optical technologies disclosed therein.

While incorporation of a resonator within an optical system can provide an improved resolution due to reduction in illumination beam size and/or detection sensitivity of the system, there are limitations on the resolution improvement that may be obtained due to divergence and losses at each internal reflection. If perfectly perpendicular-to-mirror multiple reflections existed in the resonator to support the resonance condition, the resonator would be ideal. However, due to the finite non-zero propagation distance within the resonator caused by microscopic surface variation on the mirrors, as well as by diffraction effects, the internal reflections will deviate from the ideal resonator geometrical optics model of both linear and perpendicular propagation between the mirrors.

It would therefore be desirable to improve the performance of the resonator-enhanced optical systems disclosed in the above-referenced patent applications, as well as other optical systems, in order to further improve their resolution and performance.

SUMMARY OF THE INVENTION

The foregoing objectives are achieved in an improved optical resonator apparatus and optical system having improved resolution performance along with a method for improving resolution in an optical system. The optical system includes a resonator positioned within a pathway of a measurement beam of the optical system. The resonator includes at least one imaging lens for imaging a point or area of one of the reflective surfaces of the resonator on to a point or area of a second reflective surface. The second reflective surface may be one of the resonator (resonant) surfaces, or the second reflective surface may be an intermediary surface and the resonance may be supported with respect to a single reflective surface of the resonator imaged onto itself.

Inclusion of the lens(es) reduces the optical imaging distance of the resonator to zero by imaging the two mirrors onto each other, while the propagation distance can be any chosen value. Reducing the optical imaging distance to zero improves the performance of the resonator by essentially eliminating the divergence between the multiple internal reflections.

One of the resonator reflective surfaces may be incorporated on a planar surface of the imaging lens, or provided as a separate partially reflective coated plate.

The foregoing and other objects, features, and advantages of the invention will be apparent from the following, more particular, description of the preferred embodiment of the invention, as illustrated in the accompanying drawings, wherein like reference numerals indicate like elements.

DETAILED DESCRIPTION OF ILLUSTRATIVE EMBODIMENT

The above-incorporated patent applications describe various resonator-enhanced optical systems, such as optical storage data and retrieval systems having improved data density, optical measurement systems having improved resolution and contrast, and optical systems having improved detector phase/amplitude slope characteristics controlled over portions of the detector response. The above-recited improvements are developed by placement and tuning of resonators within the optical paths of the associated systems.

The present invention concerns a method and resonator apparatus that further improve performance of a resonator-enhanced optical system by incorporating one or more imaging lenses within the resonator, causing the resonance at a single point (in practice, a very small area) or region on one or more of the reflective surfaces forming the resonator.

The present invention therefore provides an improvement in all of the above-mentioned resonator-enhanced systems, as well as other systems incorporating resonators where improved resonant performance at a particular detection point is desirable. Imaging a resonance over a very small area (point) has another advantage, in that sensitivity to surface tilt is dramatically reduced (in theory, for a single point on a surface, surface tilt is irrelevant).

Figure 1:
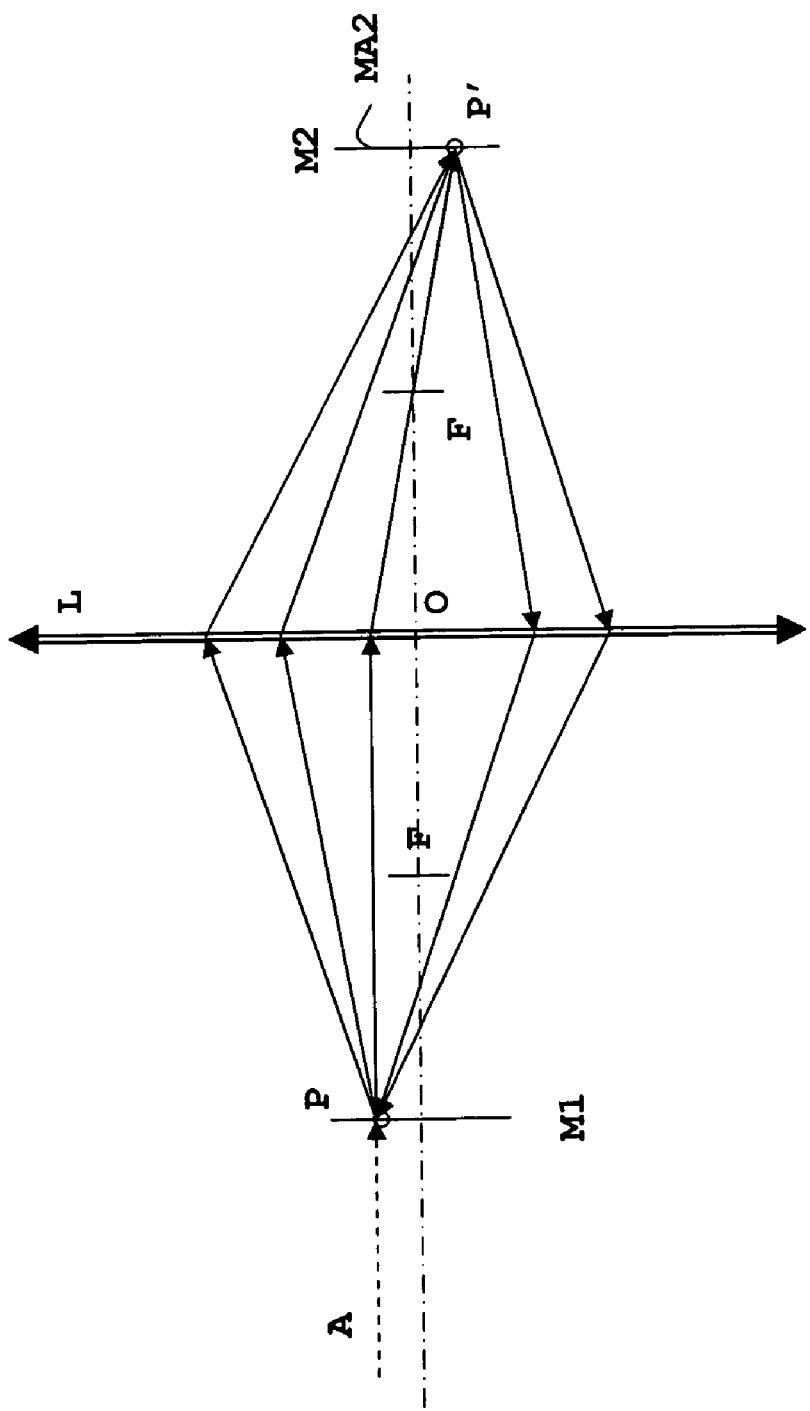
FIG. 1 is an optical schematic depicting a resonator in accordance with an embodiment of the invention.

With reference now to the figures, and particularly to FIG. 1, an optical schematic of a resonator in accordance with an embodiment of the invention is illustrated. Resonance is supported between mirrors M1 and M2. At least one of mirrors M1 and M2 is generally partially reflective, to allow coupling to the exterior of the cavity formed between mirrors M1 and M2. A lens L images the mirrors M1 and M2 onto each other (for exemplary purposes, a 1:1 magnification is illustrated). Any ray A illuminating mirror M1 at the point P provides a partially transmitted ray that is collected by lens L and imaged from point P of mirror M1 at point P' of mirror M2. Beams reflected from point P' return through lens L to mirror M1 and are imaged at location P. The reflections are supported over an angular space that reaches to the angle (in actuality forming a cone) where a larger angle ray will not be collected by lens L. Other rays introduced at points other than P and/or P' will establish a resonance between two corresponding points on the mirrors M1 and M2 within the field of view of lens L. Mirrors M1 and M2 form a resonant optical cavity that is also an imaging system. Each object/image point pair within a field of view of lens L1 resonates independently from all other points within the limitations of the resolution of lens L1. Lens L1 thus produces a "resonant image" between the two mirrors. Illumination can be spatially coherent or provided from a finite source. The resonant image described above can be coupled outside of the cavity through either (or both) of mirrors M1 and M2 and projected or imaged by known techniques onto a detector, camera, eyepiece, or other vision system.

When one of mirrors M1 or M2 is a surface of interest (e.g., the surface of interest is coated with a reflective coating), or a target/object surface, amplitude and phase at the surface of interest will be accurately reproduced at the other mirror due to the resonance effect. The amplitude and phase matching greatly increases spatial as well as height resolution distribution of the field in the object mirror (or surface of interest) that is reproduced at the image mirror. An optional mask MA2 may be incorporated into or placed directly in front of one of mirrors M1 or M2 (in the exemplary illustration mirror M2). The image on mask MA2 (such as a photo-lithographic image) will be reproduced at mirror M1 and due to the resonance established between mirror M1 and mirror M2, the image will be reproduced with virtually no degradation.

Figure 2B:
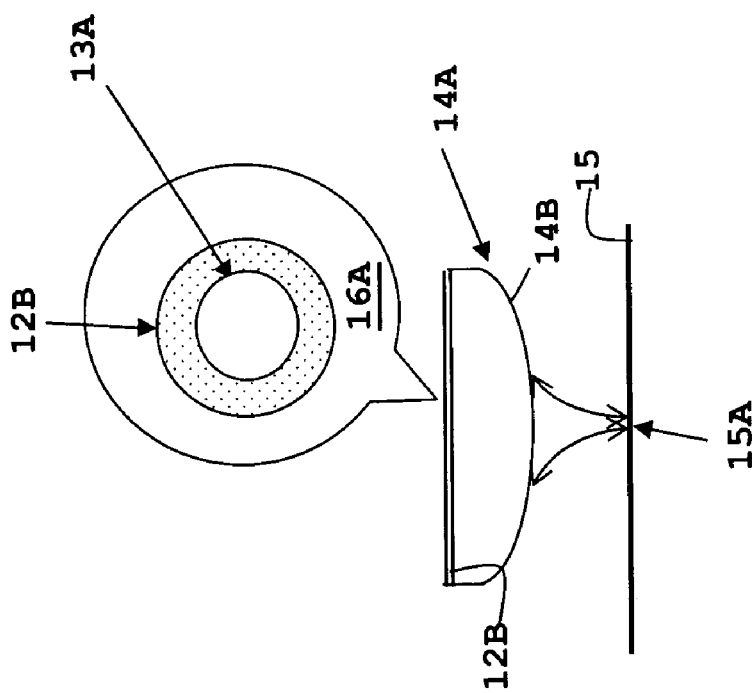
FIG. 2B is an illustration depicting an optical resonator in accordance with a second resonator embodiment of the invention.
Figure 2A:
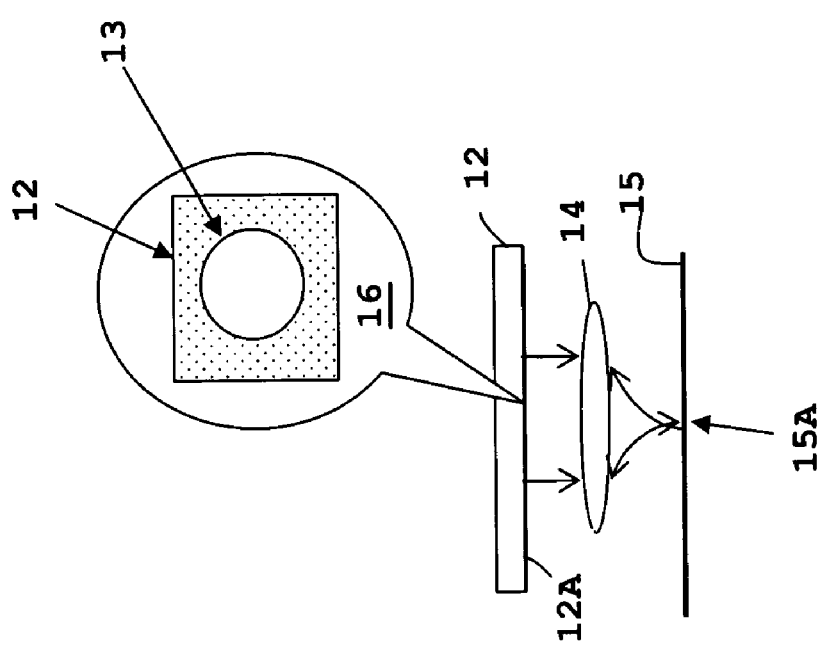
FIG. 2A is an illustration depicting an optical resonator in accordance with a first resonator embodiment of the invention.

With reference now to the other figures, and particularly to FIG. 2A, a cross section of a resonator in accordance with an embodiment of the invention is depicted. The depicted embodiment is used in systems where illumination is provided from a coherent collimated source (e.g., source at an infinite distance/infinite conjugation ratio). In the configuration of FIG. 2A, all incoming rays are parallel to the optical axis of the system. The resonator includes a partially reflective surface 12A shown as a coating deposited on a plate 12 and a second surface, which is generally a surface under observation for inspection, data detection or may be a second partially or fully reflective surface where it is useful to produce a resonant behavior at a particular point 15A. An imaging lens 14 is situated within the resonator to image surface 12A onto a surface of interest 15. For a Gaussian beam, the above-mentioned condition is achieved when both surfaces 12A and 15 are located in the two focal planes of lens 14. In the configuration of FIG. 2A, illumination introduced through partially reflective surface 12A and plate 12 is focused at point 15A and point 15A is imaged across an area of partially reflective surface 12A Area 13 of partially reflective surface 12A is shown in balloon 16 to illustrate the generally circular profile of the image area of point 15A.

Partially reflective surface 12A is positioned at a distance above point 15A such that a resonance is produced by multiple internal reflections between point 15A and partially reflective surface 12A taking into account the differing optical path length through lens 14 from a resonator without a lens. The resonator of FIG. 2A generally has the same level of resonance as a standard parallel plate Fabry-Perot resonator, but has advantages when resonance is introduced in a system where the resonance takes place between a large finite area and a single measuring point, such as in the inspection and data storage systems described in the above-incorporated patent applications.

In alternative to focusing lens 14 and setting the resonant distance with respect to a point on surface 15, the resonant length may be set to a distance above or below surface 15 providing the roughness filtering features and height sensitive improved region described in "OPTICAL INSPECTION METHOD AND APPARATUS HAVING AN ENHANCED HEIGHT SENSITIVITY REGION AND ROUGHNESS FILTERING", with consequent improvement of imaging at a point by introducing an imaging lens to produce an optical system in accordance with the present invention. Since the focal depth of lens 14 is generally much larger than the optical distances between resonant points of resonator 10, the resonant length may be adjusted by 10 or more resonances without significantly defocusing the image of point 15A. The ability to independently adjust resonant length without affecting the focus, permits filtering in accordance with the above-referenced roughness filtering techniques, as well as the enhanced phase measurements of the above-incorporated application entitled "OPTICAL MEASUREMENT AND INSPECTION METHOD AND APPARATUS HAVING ENHANCED OPTICAL PATH DIFFERENCE DETECTION".

Additionally, resonators in accordance with embodiments of the present invention may image a point on one reflective surface to another point on another reflective surface, an area on one reflective surface to an area on another reflective surface, as well as the depicted point to area imaging. Point-to-point imaging is useful for eliminating sensitivity to adjustment (tilt) of all surfaces, while point-to-area is useful for desensitizing the system on the area resonant side, while area-to-area (which is really many point to many point correspondence) is useful for image sensing (visual imaging or field imaging) or projection (as in mask projection for photolithography) as opposed to point measurement, which is generally used for phase coherent point detection measurements.

The effect of imaging lens 14 is to make the optical distance between point 15A and partially reflective surface 12A zero, by providing a convergence that counters the propagation divergence that would otherwise occur in the illumination and return paths of a beam introduced through partially reflective surface 12A and reflected from point 15A back to partially reflective surface 12A. Without the use of lens 14, existing systems generally need to use very short distances between resonator surface in both the systems described in the above-incorporated patent applications and in other resonator-enhanced optical systems. Especially when using a resonant system to detect small features of surface 15, a small propagation distance is needed, as the divergence through the resonator determines the resolution of the system within the diffraction limitations of the other optics. While confocal resonators have been implemented in existing systems that can provide enhanced resonance at a point within the resonator, when inspecting (or reading data from a surface) and using the surface as one of the resonator plates, confocal resonance is not practical, as the surface being observed is not generally a focal curve, and if it is, a particular curved matching resonator element would have to be used to achieve a confocal resonator.

The resonant path in the above-described resonator can be set to the path between point 15A and partially reflective surface 12A, or the resonance may be produced by the total path from partially reflective surface 12A through imaging lens 14 to point 15A and back through imaging lens 14 to partially reflective surface 12A. In addition to the point-focused resonator embodiments described above, the lens inside the resonator may also be adjusted to image an area of one reflective surface onto another surface, providing an imaging capability.

Sensitivity of the resonator of the present invention is not critical with respect to lens 14 or partially reflective surface 12A. Due to the Image-Object relationship generated by lens 14, the positioning of the lens is less critical than the positioning of the resonator plates. Likewise, the sensitivity to aberration or other defects in lens 14 is low, since the resonance is between point 15A and partially reflective surface 12A, and therefore the defects of lens 14 will not resonate. The resonator is most sensitive to point 15A, which is desired in systems designed to optically observe a point (or small region). Sensitivity at partially reflective surface 12A is also generally low, as the resonance that is generated between point 15A and partially reflective surface 12A is spread over area 13.

Imaging lens 14 can also be of any magnification or demagnification since the lens system transfer function is bi-univocal (i.e., having a point to point unique spatial transformation). Thus, both focusing systems (imaging at infinity—infinite conjugation ratio) for observing a point 15A as described above can be implemented, as well as finite conjugation ratio systems for imaging a fixed area onto partially reflective surface 12A can be implemented. Detailed descriptions will be provided in the exemplary embodiments described below.

An alternative embodiment of a resonator in accordance with the present invention is of particular interest, which is illustrated in FIG. 2B. A partially reflective surface 12B deposited on a lens 14A having a convex surface 14B is used in a similar fashion as the resonator of FIG. 2B and is configured to image point 15A on area 13A (shown in balloon 16A) of partially reflective surface 12B. The advantage of the resonator of FIG. 1B is that partially reflective surface 12B and lens 14A are provided as one assembly, although it is no longer possible to separately set the focal point of lens 14A at point 15A independent of the resonant wavelength of the resonator.

Both embodiments of the resonator depicted in FIGS. 2A and 2B are applicable in the systems described below, although resonators having a separate partially reflective surface and lens will be described, it should be understood that within the limitation stated above for the tunability, either configuration may be used.

Figure 2C:
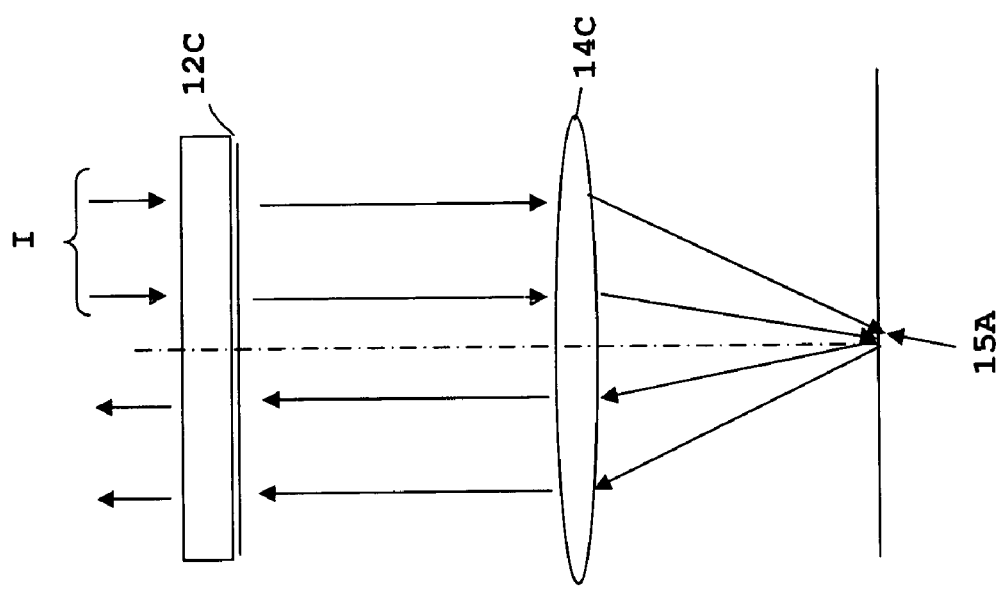
FIG. 2C is an illustration depicting an optical resonator in accordance with a third resonator embodiment of the invention.

Another possible configuration for an infinite conjugation ratio implementation is illustrated in the FIG. 2C. In the illustrated configuration, an illumination I is parallel but offset relative to the optical axis of the system. Due to the imaging properties of the system, rays bounce forth and back between two areas of partially reflective mirror 12C, supporting a resonance. In the depicted configuration, lens 14C is acting as a relay, imaging mirror 12C onto the surface, then again with an offset, imaging surface onto mirror 12C. Reflection continues, supporting resonance. An advantage of the implementation of FIG. 2C is the use of a single mirror for both reflection end-points of the resonator, a lateral offset that allows detection set apart from an incident laser beam, and a lower sensitivity to misalignments due to a "perfect optical system" configuration (the source is imaged onto itself).

Figure 3:
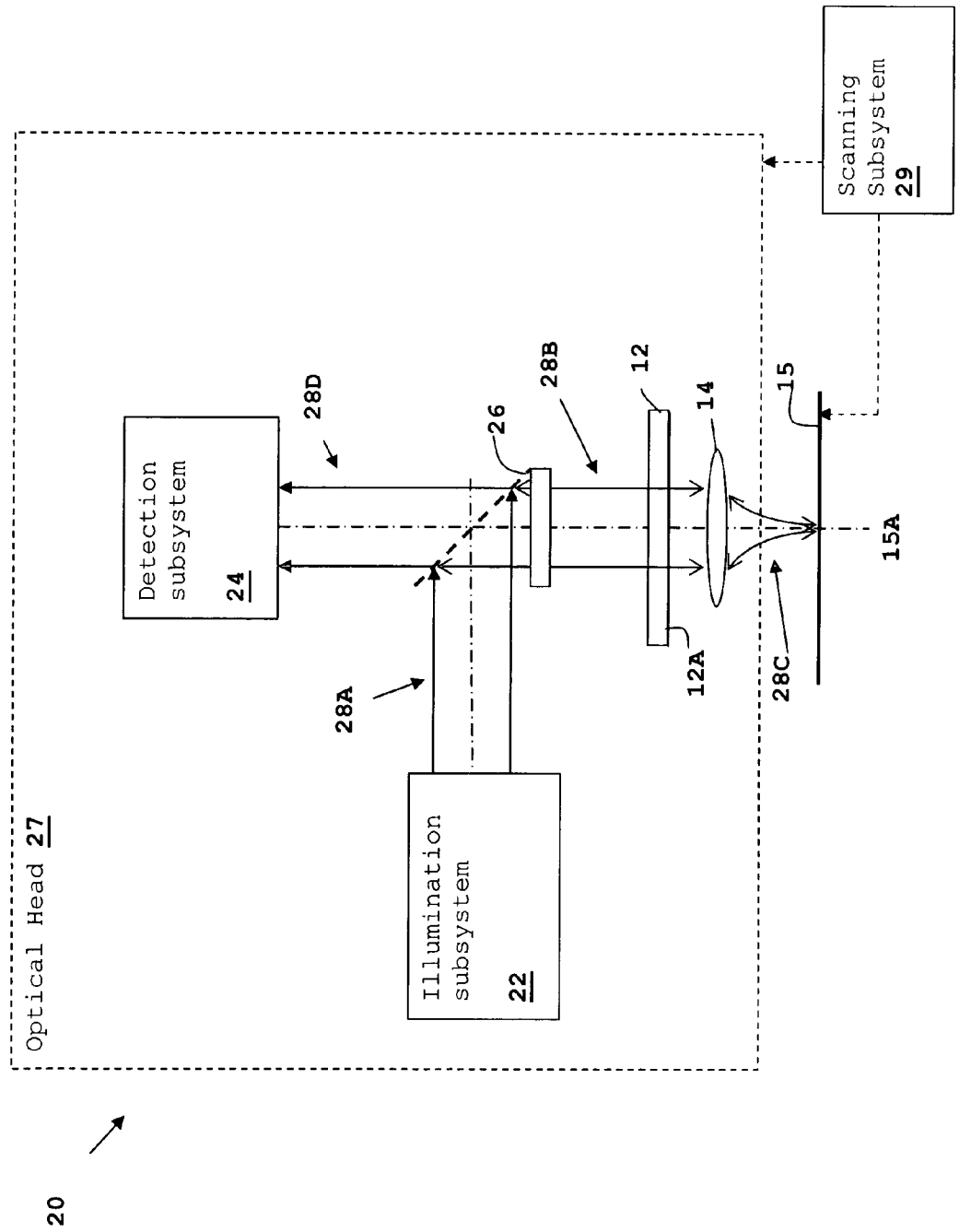
FIG. 3 is an illustration depicting an optical system incorporating a resonator in accordance with a first system embodiment of the invention.

Referring now to FIG. 3, an optical system 20 in accordance with a first system embodiment of the present invention is depicted. An illumination subsystem 22, generally a collimated laser source, is coupled to partially reflective surface 12A on plate 12 via a beamsplitter/quarter-wave plate combination 26 acting as an optical isolator. The collimated illumination beam 28A is thus directed through optical path 28B into the resonator formed by partially reflective surface 12A, imaging lens 14 and surface 15 point 15A. Within the resonator, the collimated illumination provided through optical path 28B is focused by imaging lens 14, providing point illumination at point 15A, which is then reflected by surface 15 back along optical path 28C to imaging lens 14, which images surface 15 onto partially reflective surface 12A, again through optical path 28B. The return image is then coupled through isolator/beamsplitter 26 through optical path 28D into detection subsystem 24 which can measure the phase and/or amplitude of the returned image of point 15A.

System 20 has a resonance supported by surface 15 point 15A and its image on partially reflective surface 12A. The optical path length between point 15A and partially reflective surface 12A is set so that the multiple internal reflections arriving at partially reflective surface 12A constructively interfere as the optical path length between point 15A and its image is a multiple of a half-wavelength of the illumination provided by illumination subsystem 22, as the total return path is twice the optical path length between point 15A and its image on partially reflective surface 12A.

A scanning subsystem 29, mechanically coupled to surface 15 and/or optical head 27 containing all or some of optical system 20 components can be used to scan point 15A over surface 15 providing for surface 15 inspection or data extraction from an optical media comprising surface 15.

Figure 4:
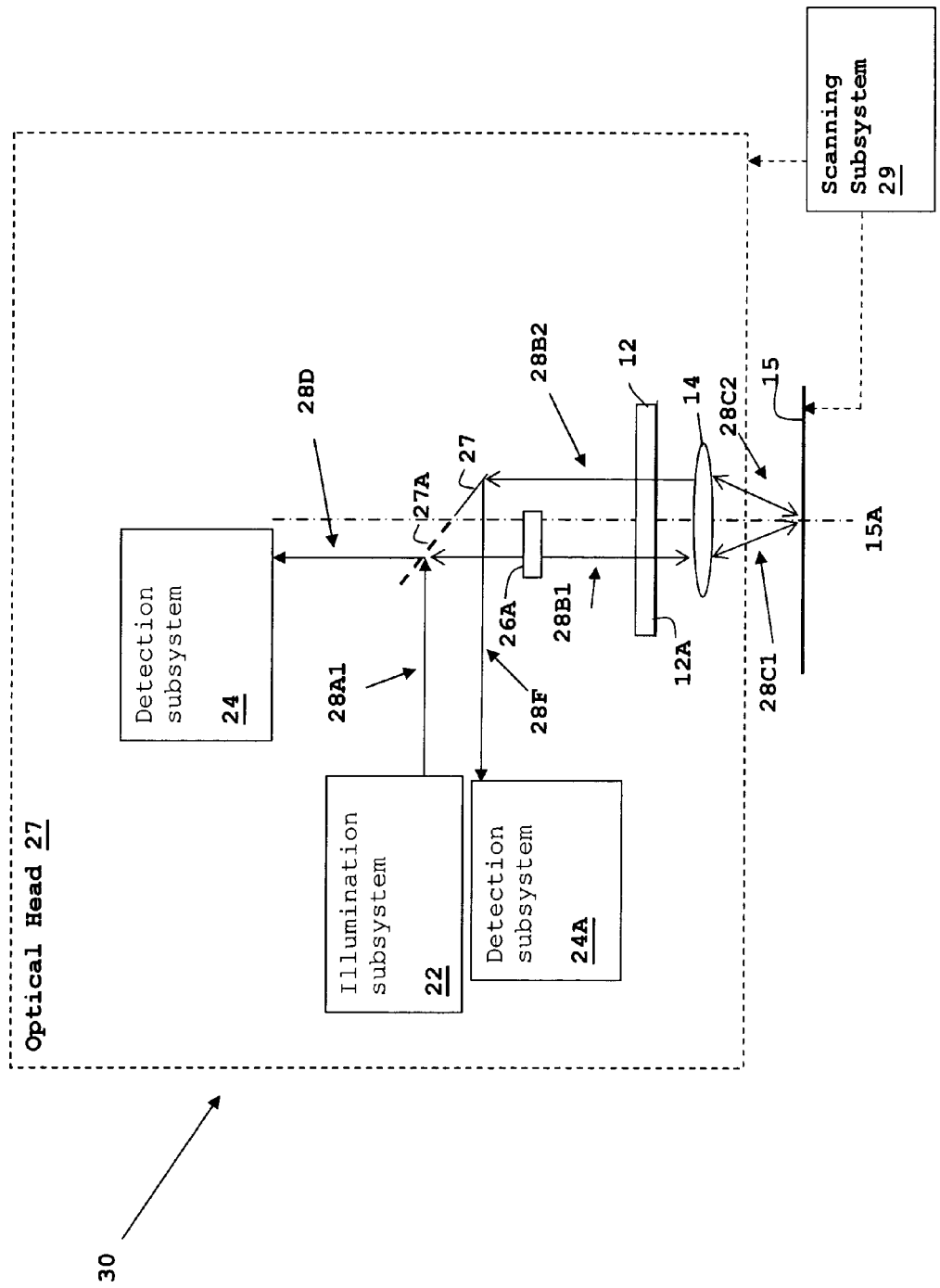
FIG. 4 is an illustration depicting an optical system incorporating a resonator in accordance with a second system embodiment of the invention.

Referring now to FIG. 4, an optical system 30, in accordance with a second system embodiment of the present invention is shown. System 30 is similar to the above-described system 20, so that only differences in structure and operation will be described below. In contrast to system 20 of FIG. 3 (and similar to that depicted in FIG. 2C) in system 30, an illumination is offset with respect to a detection path. Illumination path 28A1 is directed at a partially reflective region 27A of a mirror 27 and illumination proceeds along optical path 28B1 to lens 14.

Optical path 28C1 between imaging lens 14 and point 15A is then angled by imaging lens 14 at point 15A surface 15. The reflection from point 15A returns along optical paths 28C1 and 28C2 and is imaged by imaging lens 14 onto partially reflective surface 12A. Light reflected back on optical path 28C1 returns along optical path 28B1 and sent by quarter-wave plate 26A and mirror 27 (via beam-splitting region 27A) to a detection subsystem 24 along optical path 28D, while light reflected along optical path 28C2 returns along an optical path 28B2 at a offset equal to and opposite side of the optical axis of lens 14 from optical path 28B1. Detection subsystem 24A receives the returned image of point 15A along optical path 28B2 and measures the returned light from optical path 28F via reflection of the fully-reflective portion of mirror 27. Due to the conservation of energy within optical system 30, the light detected by detection subsystems 24 and 24A will be complementary in amplitude.

Within the resonator, the illumination provided through optical path 28B1 is focused by imaging lens 14, providing off-axis point illumination at point 15A, which is then reflected by surface 15 back along optical paths 28C1 and 28C2 to imaging lens 14, and images the reflection onto partially reflective surface 12A, through optical paths 28B1 and 28B2. System 30 has a resonance supported twice by areas (which may overlap or be separate, depending on the scale of system 30 and the image sport size) on partially reflective surface 12A via a reflection imaged through lens onto point 15A of surface 15 and back to partially reflective surface 12A. Surface 15 acts as an intermediary reflective surface and not as a resonant surface within the resonator. As in system 20 of FIG. 3, the resonant optical path length between point 12A and itself is set so that multiple internal reflections arriving at partially reflective surface 12A constructively interfere, that is, the optical path length between point 15A and partially reflective surface 12A is still a multiple of a half-wavelength of the illumination provided by illumination subsystem 22, as the total path from partially reflective surface to point 15A and back is twice the optical path length between point 15A and its image on partially reflective surface 12A as described in FIG. 1.

Figure 5:
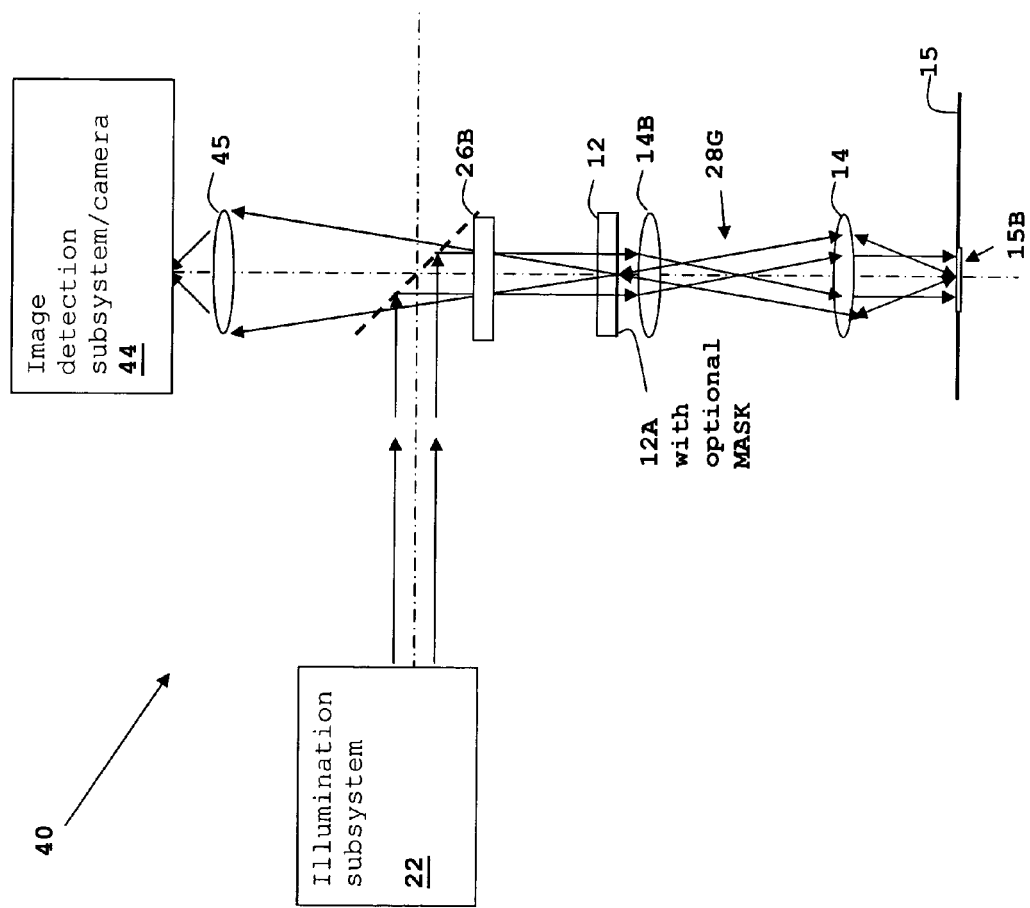
FIG. 5 is an illustration depicting an optical system incorporating a resonator in accordance with a third system embodiment of the invention.

Referring now to FIG. 5, an optical system 40, in accordance with a third system embodiment of the present invention is shown. System 40 may also include a mechanical or electromechanical scanning system as depicted in FIGS. 1 and 2, but is omitted for clarity of depiction. System 40, rather than imaging a point on surface 15, images an area 15B onto an area of partially reflective surface 12A, providing an image of each point within area 15B imaged to a corresponding point on partially reflective surface 12A. In order to improve illumination by removing the image of the source from the object plane, a second lens, focusing lens 14B, is added to the resonator. Illumination is provided from illumination subsystem 22 through an isolator 26B as used above in system 20.

Imaging lens 14 images a reflection of a point in area 15B into a converging beam in optical path 28G onto a corresponding point on surface 12. Lens 14B is a field lends that provides good coverage of the resonating field of view. A third lens 45 outside of the resonator, images partially reflective surface 12A onto detection subsystem 44. Thus the third depicted embodiment is a system 40 capable of visual observation by a purely optical system (inspection microscope) as well as electro-optical imaging systems.

Resonance is supported between the area on partially reflective surface 12A and area 15B on surface 12, so that multiple optical path length between area 15B and partially reflective surface 12A is set so that the multiple internal reflections arriving at partially reflective surface 12A constructively interfere and the multiple internal reflections arriving at area 15B constructively interfere, as the optical path length between each point in area 15B and the corresponding point on partially reflective surface 12A is a multiple of a half-wavelength of the illumination provided by illumination subsystem 22. Partially reflective surface 12A may include an optional mask as described above with reference to FIG. 1, for reproducing an image of the mask at area 15B. The resonance of the system provides for near-perfect reproduction of the mask at area 15B.

An advantage of the finite conjugation ration system 40 depicted in FIG. 5, is that system 40 has a low sensitivity to adjustments, as well as the ability to measure images rather than single points.

Any of the above-described structures can be used to provide multiple cascaded resonators by using multiple lens-enhanced resonators and/or non-lens resonators in combination. Further, a mask can be incorporated within any of the above systems for reproducing an image of the mask on another surface. The partially reflective surface can be placed as close to the optics as need or can be incorporated in the optics as shown in the resonator of FIG. 1B. In the imaging system of FIG. 4, the partially reflective surface may be provided as a coating on a planar side of a plano-convex focusing lens (as opposed to a coating on the imaging lens).

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. An optical resonator comprising:
   multiple reflective surfaces for sustaining multiple internal reflections in a cavity formed between said reflective surfaces; and
   an imaging lens positioned at a predetermined position along an optical path between a first and second one of said multiple reflective surfaces and having a predetermined focal length such that a first region on said first reflective surface is imaged onto a second region on said second reflective surface.

2. The optical resonator of claim 1, wherein a focal length of said imaging lens is a predetermined focal length, wherein a focal point of said imaging lens is predetermined to intersect said second reflective surface, whereby said second region approximates a point.

3. The optical resonator of claim 2, wherein focal lengths of said imaging lens are predetermined focal lengths such that focal points of said imaging lens are predetermined to intersect said second reflective surface on a first side of said imaging lens and said first reflective surface on a second side of said imaging lens, whereby said first region and said second region approximate points.

4. The optical resonator of claim 1, wherein said imaging lens is positioned and a focal length of said imaging lens is a predetermined focal length such that, focal points of said imaging lens are predetermined to fall substantially beyond said first reflective surface and said second reflective surface, whereby said first region is an area of said first reflective surface and said second region is an area of said second reflective surface.

5. The optical resonator of claim 4, wherein said first reflective surface and said second reflective surface are positioned such that an optical path length between a first set of points comprising said first region and corresponding points of a second set of points within said second region is a multiple of one-half of a predetermined optical wavelength.

6. The optical resonator of claim 5, further comprising a focusing lens positioned between said imaging lens and said first reflective surface for focusing an image of a point within said second region of said second reflective surface on a point within said first region of said first reflective surface.

7. The optical resonator of claim 1, wherein said first reflective surface and said second reflective surface are positioned such that an optical path length between first set of points comprising said first region and corresponding points of a second set of points of a third region displaced from said second region is a multiple of one-half of a predetermined optical wavelength, whereby surface features of said second reflective surface approaching or intersecting said third region resonate with said first reflective surface, while surface features not approaching or intersecting said third region do not resonate with said first reflective surface at a predetermined optical wavelength.

8. The optical resonator of claim 1, wherein said imaging lens is a plano-convex lens having a planar surface and an opposing convex surface, wherein said first reflective surface is a partially reflective surface formed by a partially reflective coating deposited on said planar surface of said imaging lens.

9. The optical resonator of claim 1, wherein said imaging lens is a plano-convex lens having a planar surface and an opposing convex surface, wherein said first reflective surface is a substantially totally reflective surface formed by a substantially totally reflective coating deposited on said planar surface of said imaging lens.

10. The optical resonator of claim 1, further comprising a mask positioned at said first reflective surface, whereby said mask is imaged onto said second reflective surface by said imaging lens.

11. An optical system for detecting features of a surface of interest, said system comprising:
an illumination subsystem for producing an illumination beam;
a detection subsystem for detecting a beam reflected from said surface of interest; and
a resonator positioned in an optical path between said surface under observation and said illumination subsystem for increasing an effective resolution of said detection subsystem, said resonator comprising
multiple reflective surfaces, including at least said surface of interest and at least one other reflective surface for sustaining multiple internal reflections in a cavity formed between said reflective surfaces, and
an imaging lens positioned at a predetermined position along an optical path between said at least one other reflective surface and said surface of interest and having a predetermined focal length such that a first region on said at least one other reflective surface is imaged onto a second region on said surface of interest.

12. The optical system of claim 11, wherein said surface of interest comprises a surface of an optical storage media, and wherein said detection subsystem includes a data detection block for detecting data stored on said optical storage media.

13. The optical subsystem of claim 11, wherein said surface of interest is a surface under inspection, wherein said detector detects surface variations of said surface under inspection and wherein a minimum feature size of detectable surface variations is decreased by action of said resonator.

14. The optical system of claim 11, further comprising a scanning subsystem for mechanically moving one of said surface of interest or said resonator relative to the other, whereby features of said surface of interest are detected by said detection subsystem.

15. The optical system of claim 11, wherein a focal length of said imaging lens is a predetermined focal length, wherein a focal point of said imaging lens is predetermined to intersect said surface of interest, whereby said second region approximates a point.

16. The optical system of claim 15, wherein focal lengths of said imaging lens are predetermined focal lengths such that focal points of said imaging lens are predetermined to intersect said surface of interest on a first side of said imaging lens and said at least one other reflective surface on a second side of said imaging lens, whereby said first region and said second region approximate points.

17. The optical system of claim 11, wherein said imaging lens is positioned and a focal length of said imaging lens is a predetermined focal length such that, focal points of said imaging lens are predetermined to fall substantially beyond said at least one other reflective surface and said surface of interest, whereby said first region is an area of said at least one other reflective surface and said second region is an area of said surface of interest.

18. The optical system of claim 11, wherein said at least one other reflective surface and said surface of interest are positioned such that an optical path length between a first set of points comprising said first region and corresponding points of a second set of points within said second region is a multiple of one-half of a predetermined optical wavelength.

19. The optical system claim 11, further comprising a focusing lens positioned between said imaging lens and said first reflective surface for focusing an image of points within said second region of said surface of interest on corresponding unique points within said first region of said at least one other reflective surface.

20. The optical system of claim 11, wherein said at least one other reflective surface and said surface of interest are positioned such that an optical path length between first set of points comprising said first region and corresponding points of a second set of points of a third region displaced from said second region is a multiple of one-half of a predetermined optical wavelength, whereby surface features of said surface of interest approaching or intersecting said third region resonate with said at least one other reflective surface, while surface features not approaching or intersecting said third region do not resonate with said at least one other reflective surface at a predetermined optical wavelength.

21. The optical system of claim 11, wherein said imaging lens is a plano-convex lens having a planar surface and an opposing convex surface, wherein said at least one other reflective surface is a partially reflective surface formed by a partially reflective coating deposited on said planar surface of said imaging lens.

22. The optical system of claim 11, further comprising a mask positioned at said at least one other reflective surface, whereby said mask is imaged at said second region by said imaging lens.

23. A method improving resolution of a resonator-enhanced optical system, said method comprising:
reflecting light between multiple parallel reflective surfaces to provide multiple internal reflections; and
imaging a first region of a first one of said reflective surfaces on a second region of a second one of said reflective surfaces with an imaging lens, whereby a divergence of said multiple internal reflections is reduced, improving said resolution.

24. The method of claim 23, wherein said first reflective surface is a partially reflective surface and said second reflective surface is a surface of interest, and wherein said method further comprises:

scanning said surface of interest and said first reflective surface relative to each other; and detecting light emitted from said first reflective surface produced by reflections from said surface of interest, whereby a minimum detectable size of features of said surface of interest is decreased by action of said imaging.

25. The method of claim 23, wherein a focal length of said imaging lens is a predetermined focal length, wherein a focal point of said imaging lens is predetermined to intersect said second reflective surface, whereby said second region approximates a point and wherein said imaging images said point on an area of said first reflective surface.

26. The method of claim 23, wherein said imaging lens is positioned and a focal length of said imaging lens is a predetermined focal length such that focal points of said imaging lens are predetermined to fall substantially beyond said first reflective surface and said second reflective surface, wherein said imaging images a first area on said first reflective surface to a second area of said second reflective surface.

27. The method of claim 26, further comprising focusing said multiple reflections through a focusing lens positioned between said imaging lens and said first reflective surface to image points within said second region of said second reflective surface on corresponding unique points within said first region of said first reflective surface.

28. The method of claim 23, further comprising, masking light reflected at one of said multiple parallel reflective surfaces, whereby an image produced by said masking is imaged by said imaging at another one of said multiple parallel reflective surfaces.

* * * * *